United States Patent
Nakagawa et al.

(10) Patent No.: US 9,162,936 B2
(45) Date of Patent: *Oct. 20, 2015

(54) METHOD FOR MANUFACTURING HYDROCARBON

(71) Applicant: TOYODA GOSEI CO., LTD., Kiyosu-shi, Aichi-ken (JP)

(72) Inventors: Hiroyuki Nakagawa, Kiyosu (JP); Seitaro Taki, Kiyosu (JP); Hisashi Mizuno, Kiyosu (JP)

(73) Assignee: TOYODA GOSEI CO., LTD., Aichi-pref. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/361,709

(22) PCT Filed: Jan. 17, 2013

(86) PCT No.: PCT/JP2013/050789
§ 371 (c)(1),
(2) Date: May 30, 2014

(87) PCT Pub. No.: WO2013/108833
PCT Pub. Date: Jul. 25, 2013

(65) Prior Publication Data
US 2015/0126630 A1      May 7, 2015

(30) Foreign Application Priority Data

Jan. 20, 2012   (JP) ................................. 2012-051253

(51) Int. Cl.
*C07C 27/06*   (2006.01)
*C07C 1/12*   (2006.01)

(52) U.S. Cl.
CPC ........................................ *C07C 1/12* (2013.01)

(58) Field of Classification Search
CPC .......................................................... C10G 2/50
USPC ......................................................... 518/702
See application file for complete search history.

(56) References Cited

U.S. PATENT DOCUMENTS 7,883,805 B2 *   2/2011   Nakai et al. ................... 429/416
2008/0051478 A1   2/2008   Tran et al.

FOREIGN PATENT DOCUMENTS

| CN | 101773833 A | 7/2010 |
| JP | 55-105625 A | 8/1980 |
| JP | 60-197238 A | 10/1985 |
| JP | 08-127544 A | 5/1996 |
| JP | 09-124515 A | 5/1997 |
| JP | 2000-344689 A | 12/2000 |
| JP | 2004-505879 A | 2/2004 |
| JP | 2008-150289 A | 7/2008 |
| JP | 2009-034654 A | 2/2009 |
| JP | 2010-022944 A | 2/2010 |

OTHER PUBLICATIONS

The International Preliminary Report on Patentability mailed on Jul. 31, 2014 for the priority application No. PCT/JP2012/051253 (with English translation).
The International Preliminary Report on Patentability mailed on Jul. 31, 2014 for the corresponding International application No. PCT/JP2013/050789 (with English translation).
Jung-Nam Park et al., A highly dispersed Pd-Mg/SiO$_2$ catalyst active for methanation of CO$_2$, Journal of Catalysis, Aug. 15, 2009, vol. 266, No. 1, pp. 92-97.
International Search Report mailed Mar. 12, 2013 for the corresponding international application No. PCT/JP2013/050789 (with English translation).

* cited by examiner

*Primary Examiner* — Sudhakar Katakam
(74) *Attorney, Agent, or Firm* — Posz Law Group, PLC (57) ABSTRACT

It is to provide a method for manufacturing a hydrocarbon, with which a hydrocarbon is produced at a high yield even under the condition of an ordinary temperature and an ordinary pressure.
A method for manufacturing a hydrocarbon, in which carbon dioxide is reduced to produce the hydrocarbon, the method includes a step of producing the hydrocarbon by bringing magnesium or a magnesium compound such as magnesium oxide into contact with water and the carbon dioxide and reducing the carbon dioxide. Examples of the magnesium compound include magnesium oxide, magnesium hydroxide, magnesium carbonate, and basic magnesium carbonate.

14 Claims, 1 Drawing Sheet

METHOD FOR MANUFACTURING HYDROCARBON

CROSS REFERENCE TO RELATED APPLICATIONS

This application is a U.S. national stage application of PCT/JP2013/050789 filed on Jan. 17, 2013, and claims priority to, and incorporates by reference, International Patent Application No. PCT/JP2012/051253 filed on Jan. 20, 2012.

TECHNICAL FIELD

The present invention relates to a method for manufacturing a hydrocarbon by reducing carbon dioxide.

BACKGROUND

Conventional methods for obtaining a hydrocarbon such as methane by reducing carbon dioxide include a method described in Patent Document 1 in which hydrogen gas is used as a hydrogen source under the reaction condition of a high temperature (150° C. to 400° C.) and a high pressure (1 MPa to 6 MPa). However, this method requires such a reaction condition of a high temperature and a high pressure, and thus the reaction equipment becomes complicated, leading to high cost, for example.

In contrast, as a method that is conducted under the condition of an ordinary temperature and an ordinary pressure and requires no hydrogen gas as a hydrogen source, Patent Document 2 describes a method that uses iron powder as a catalyst to obtain a hydrocarbon such as methane from carbon dioxide and water.

Although methods described in Patent Documents 3 and 4 produce hydrogen from particulate magnesium and water, these methods are not for obtaining a hydrocarbon such as methane by reducing carbon dioxide.

PATENT DOCUMENTS

Patent Document 1: Japanese Patent Application Publication No. 08-127544 (JP 08-127544 A)
Patent Document 2: Japanese Patent Application Publication No. 2000-344689 (JP 2000-344689 A)
Patent Document 3: Japanese Patent Application Publication No. 2008-150289 (JP 2008-150289 A)
Patent Document 4: Published Japanese Translation of PCT application No. 2004-505879 (JP-A-2004-505879)

However, in the method of Patent Document 2, methane and the like cannot be obtained as much as the amount described in Patent Document 2, and the yield of the hydrocarbon is small (see Comparative Examples 3 and 4 in Table 3).

Therefore, an object of the present invention is to provide a method for manufacturing a hydrocarbon, with which a hydrocarbon is produced at a high yield even under the condition of an ordinary temperature and an ordinary pressure.

SUMMARY

To solve the above issue, the present invention provides a method for manufacturing a hydrocarbon, in which carbon dioxide is reduced to produce the hydrocarbon. The method includes a production step of producing the hydrocarbon by bringing magnesium or a magnesium compound into contact with water and the carbon dioxide and reducing the carbon dioxide.

Figure 1:
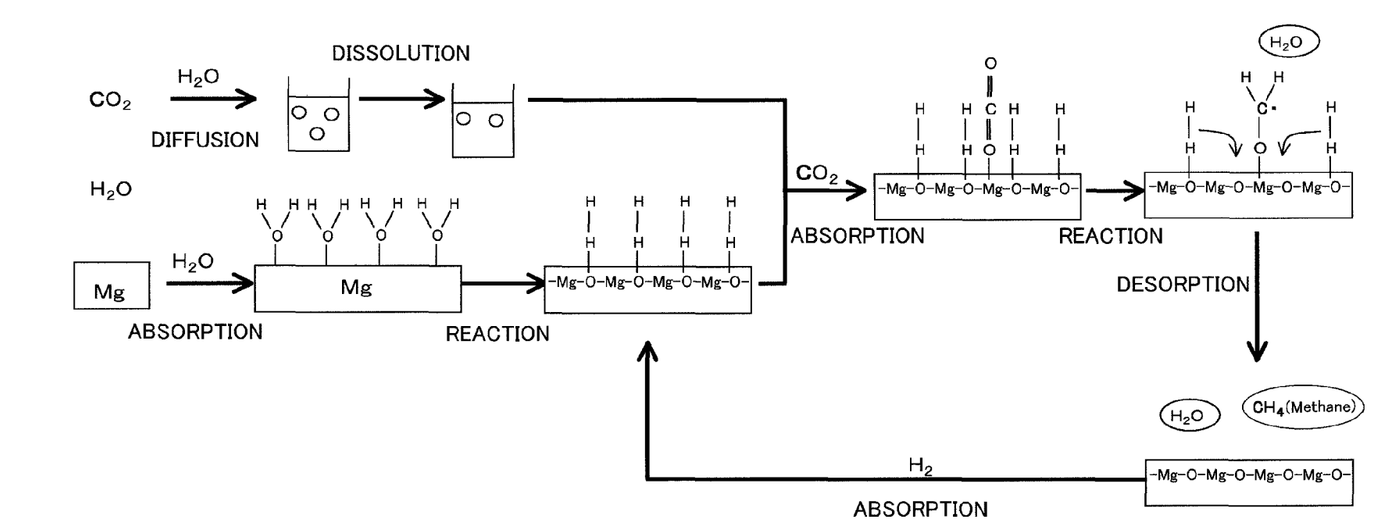
FIG. 1 is a schematic drawing of a reaction for producing methane according to the present invention.

Although the detail of the reaction in the production step has not been clarified yet, the reaction of methane is assumed to occur, for example, as shown in FIG. 1.

As shown in FIG. 1, carbon dioxide ($CO_2$) is diffused upon contact with water, and a part of the carbon dioxide is dissolved in the water ($H_2O$). Meanwhile, magnesium (Mg) brought into contact with water is reacted with the water adsorbed on the surface of the magnesium, and while being oxidized, the magnesium is in a transition state in which magnesium oxide has hydrogen. A magnesium compound brought into contact with water also reacts with the water adsorbed on the surface of the magnesium compound to generate hydrogen, and is in a transition state in which the magnesium compound has hydrogen. Then, the carbon dioxide contained in water is adsorbed on the magnesium in the transition state so that the carbon dioxide reacts with hydrogen to be reduced, thus producing methane. Finally, the produced methane ($CH_4$) is considered to be desorbed from the magnesium.

It is also considered that by bringing a magnesium compound into contact with hydrogen ($H_2$), a part of the hydrogen is adsorbed on the magnesium compound, and the magnesium compound is brought into a transition state in which the magnesium compound has hydrogen.

An aspect of each component in the method for manufacturing a hydrocarbon of the present invention will be exemplified below.

1. Production Step

The production step is not particularly limited and may be a step in which magnesium is brought into contact with water and carbon dioxide to produce a hydrocarbon, or a step in which a magnesium compound is brought into contact with water and carbon dioxide to produce a hydrocarbon.

The hydrocarbon obtained in the production step is not particularly limited. Examples thereof include alkanes such as methane, ethane, and propane, and alkenes such as ethylene and propylene.

The hydrogen is not particularly limited. The hydrogen, may be a hydrogen gas introduced in the production step, may be a hydrogen gas generated by, for example, allowing a metal having ionization tendency larger than that of hydrogen, such as magnesium and sodium, to react with the water in case where water (including water vapor) is present in the production step, or may be hydrogen generated by allowing a magnesium compound to react with water.

The production step preferably includes a stirring step of stirring with ceramic beads so that the yield of a hydrocarbon increases. With the stirring step, magnesium or a magnesium compound is crushed and ground, and thus the reactivity of the magnesium or the magnesium compound can be enhanced. If the production step is conducted in water, such stirring can reduce non-uniformity in concentrations of carbon dioxide and hydrogen in water.

The ceramic beads are not particularly limited, and examples thereof include zirconia beads and alumina beads. The particle size of the ceramic bead is not particularly limited, and, for example, is 0.1 mm to 10.0 mm.

2. Magnesium

Although the shape of the magnesium is not particularly limited, the magnesium is preferably particulate because the specific surface area is large and thus the yield of a hydrocarbon is high. The size of particulate magnesium is not particularly limited, and, for example, is 1 μm to 1000 μm.

3. Magnesium Compound

The magnesium compound is not particularly limited. Examples thereof include poorly water-soluble magnesium compounds (the solubility at 15° C. is not greater than 0.01

[g/100 g-H$_2$O]), such as magnesium oxide (MgO), magnesium hydroxide (Mg(OH)$_2$), magnesium carbonate (MgCO$_3$), and basic magnesium carbonate (Mg(OH)$_2$·MgCO$_2$).

Although the shape of the magnesium compound is not particularly limited, the magnesium is preferably particulate because the specific surface area is large and thus the yield of a hydrocarbon is high. The size of the particulate magnesium compound is not particularly limited, and, for example, is 1 µm to 1000 µm.

Effects of the Invention

The present invention can provide a method for manufacturing a hydrocarbon, with which the hydrocarbon is produced at a high yield even under the condition of an ordinary temperature and an ordinary pressure.

DETAILED DESCRIPTION

A method for manufacturing a hydrocarbon in which carbon dioxide is reduced to produce the hydrocarbon. The method includes a production step of dissolving carbon dioxide in water containing magnesium or a magnesium compound, and bringing the magnesium or the magnesium compound into contact with water and the carbon dioxide to produce the hydrocarbon.

A method for manufacturing a hydrocarbon in which carbon dioxide is reduced to produce the hydrocarbon. The method includes a production step of dissolving carbon dioxide and hydrogen in water containing a magnesium compound, and bringing the magnesium compound into contact with the water, the hydrogen, and the carbon dioxide to produce the hydrocarbon.

Examples

As examples of the present invention, firstly, reactions were conducted under 17 conditions (Example 8 was unassigned), and each of the gas components obtained after the reactions was analyzed. Tables 1 and 2 show respective conditions and results of analyses for the gas components. As comparative examples, reactions were conducted under 22 conditions, and each of the gas components obtained after the reactions was analyzed. Tables 3 and 4 show respective conditions and results of analyses for the gas components. In both examples and comparative examples, external controls for heating or cooling and for pressurization or depressurization were not performed, and reactions were conducted under the atmosphere of an ordinary temperature and an ordinary pressure. The ordinary temperature is, for example, 20° C.±15° C. (5° C. to 35° C.). The ordinary pressure is, for example, 0.1 MPa±0.05 MPa (0.05 MPa to 0.15 MPa). Note that, in columns of "Detected Gas Component After Reaction" in Tables 1 to 4, "ND" means "not detected," that is, the value is not greater than the detection limit of the analysis equipment, and "–" means no analysis was conducted.

TABLE 1

|  |  |  |  | Example 1 | Example 2 | Example 3 | Example 4 | Example 5 |
|---|---|---|---|---|---|---|---|---|
| Substances Compounded | Water (ml) |  |  | 50 | 50 | 50 | 50 | 50 |
|  | Carbon Dioxide (Injection Time) |  |  | 3 minutes | 3 minutes | 3 minutes | 3 minutes | 3 minutes |
|  | Hydrogen (Injection Time) |  |  |  |  |  |  |  |
|  | Particle Body | Mg | 414 µm | 0.1 g | 0.1 g |  |  |  |
|  |  |  | 371 µm |  |  | 0.1 g | 0.1 g | 0.1 g |
|  |  |  | 18 µm |  |  |  |  |  |
|  |  | MgO | 150 µm |  |  |  |  |  |
|  |  | Mg(OH)$_2$ | 150 µm |  |  |  |  |  |
|  |  | MgCO$_3$ | 150 µm |  |  |  |  |  |
|  |  | Mg(OH)$_2$·MgCO$_3$ | 150 µm |  |  |  |  |  |
| Reaction Condition | Still Standing | Place |  | Indoor | Outdoor | Indoor | Indoor | Indoor |
|  |  | Time |  | 14 days | 14 days | 3 days | 7 days | 14 days |
|  | Stir |  |  | no | no | no | no | no |
|  | Ceramic Beads | Zirconia 1.25 mm |  | — | — | — | — | — |
|  |  | Alumina 0.5 mm |  | — | — | — | — | — |
| Detected Gas Component After Reaction | Methane |  |  | 1400 ppm | 1500 ppm | 1500 ppm | 1600 ppm | 1900 ppm |
|  | Ethane |  |  | 6 ppm | 8 ppm | 7 ppm | 7 ppm | 7 ppm |
|  | Propane |  |  | 1 ppm | 1 ppm | 1 ppm | 1 ppm | 1 ppm |
|  | Ethylene, Propylene |  |  | 1 ppm | 3 ppm | 3 ppm | 3 ppm | 3 ppm |
|  | Carbon Monoxide |  |  | — | — | — | — | — |
|  | Hydrogen |  |  | 60% | — | — | — | — |

|  |  |  |  | Example 6 | Example 7 | Example 13 | Example 14 |
|---|---|---|---|---|---|---|---|
| Substances Compounded | Water (ml) |  |  | 50 | 50 | 50 | 50 |
|  | Carbon Dioxide (Injection Time) |  |  | 3 minutes | 1 minute | 1 minute | 1 minute |
|  | Hydrogen (Injection Time) |  |  |  |  |  |  |
|  | Particle Body | Mg | 414 µm |  |  |  |  |
|  |  |  | 371 µm | 0.1 g |  | 0.1 g | 0.1 g |
|  |  |  | 18 µm |  | 0.1 g |  |  |
|  |  | MgO | 150 µm |  |  |  |  |
|  |  | Mg(OH)$_2$ | 150 µm |  |  |  |  |
|  |  | MgCO$_3$ | 150 µm |  |  |  |  |
|  |  | Mg(OH)$_2$·MgCO$_3$ | 150 µm |  |  |  |  |

TABLE 1-continued

|  |  |  |  |  |  |  |
|---|---|---|---|---|---|---|
| Reaction Condition | Still Standing | Place | Indoor dark place | Indoor | Indoor | Indoor |
|  |  | Time | 3 days | 7 days | 3 days | 3 days |
|  | Stir |  | no | no | yes | yes |
|  | Ceramic Beads | Zirconia 1.25 mm | — | — | present | — |
|  |  | Alumina 0.5 mm | — | — | — | present |
| Detected Gas Component After Reaction | Methane |  | 1500 ppm | 2203 ppm | 6679 ppm | 6600 ppm |
|  | Ethane |  | 7 ppm | 67 ppm | 360 ppm | 360 ppm |
|  | Propane |  | 1 ppm | 1 ppm | 36 ppm | 35 ppm |
|  | Ethylene, Propylene |  | ND | 4 ppm | 31 ppm | 32 ppm |
|  | Carbon Monoxide |  | — | 28 ppm | 28 ppm | 30 ppm |
|  | Hydrogen |  | — | 22% | — | — |

TABLE 2

|  |  |  |  | Example 9 | Example 10 | Example 11 | Example 12 |
|---|---|---|---|---|---|---|---|
| Substances Compounded | Water (ml) |  |  | 50 | 50 | 50 | 50 |
|  | Carbon Dioxide (Injection Time) |  |  | 3 minutes | 3 minutes | 3 minutes | 3 minutes |
|  | Hydrogen (Injection Time) |  |  | 3 minutes | 3 minutes | 3 minutes | 3 minutes |
|  | Particle Body | Mg | 414 μm |  |  |  |  |
|  |  |  | 371 μm |  |  |  |  |
|  |  |  | 18 μm |  |  |  |  |
|  |  | MgO | 150 μm | 0.1 g |  |  |  |
|  |  | Mg(OH)$_2$ | 150 μm |  | 0.1 g |  |  |
|  |  | MgCO$_3$ | 150 μm |  |  | 0.1 g |  |
|  |  | Mg(OH)$_2$·MgCO$_3$ | 150 μm |  |  |  | 0.1 g |
| Reaction Condition | Still Standing | Place |  | Indoor | Indoor | Indoor | Indoor |
|  |  | Time |  | 7 days | 7 days | 7 days | 7 days |
|  | Stir |  |  | no | no | no | no |
|  | Ceramic Beads | Zirconia 1.25 mm |  | — | — | — | — |
|  |  | Alumina 0.5 mm |  | — | — | — | — |
| Detected Gas Component After Reaction | Methane |  |  | 30 ppm | 50 ppm | 30 ppm | 30 ppm |
|  | Ethane |  |  | 3 ppm | 3 ppm | 3 ppm | 3 ppm |
|  | Propane |  |  | 1 ppm | 1 ppm | 1 ppm | 1 ppm |
|  | Ethylene, Propylene |  |  | ND | ND | ND | 3 ppm |
|  | Carbon Monoxide |  |  | — | — | — | — |
|  | Hydrogen |  |  | — | — | — | — |

|  |  |  |  | Example 15 | Example 16 | Example 17 | Example 18 |
|---|---|---|---|---|---|---|---|
| Substances Compounded | Water (ml) |  |  | 50 | 50 | 50 | 50 |
|  | Carbon Dioxide (Injection Time) |  |  | 1 minute | 1 minute | 1 minute | 1 minute |
|  | Hydrogen (Injection Time) |  |  | 1 minute | 1 minute | 1 minute | 1 minute |
|  | Particle Body | Mg | 414 μm |  |  |  |  |
|  |  |  | 371 μm |  |  |  |  |
|  |  |  | 18 μm |  |  |  |  |
|  |  | MgO | 150 μm | 0.1 g |  |  |  |
|  |  | Mg(OH)$_2$ | 150 μm |  | 0.1 g |  |  |
|  |  | MgCO$_3$ | 150 μm |  |  | 0.1 g |  |
|  |  | Mg(OH)$_2$·MgCO$_3$ | 150 μm |  |  |  | 0.1 g |
| Reaction Condition | Still Standing | Place |  | Indoor | Indoor | Indoor | Indoor |
|  |  | Time |  | 3 days | 3 days | 3 days | 3 days |
|  | Stir |  |  | yes | yes | yes | yes |
|  | Ceramic Beads | Zirconia 1.25 mm |  | present | present | present | present |
|  |  | Alumina 0.5 mm |  | — | — | — | — |
| Detected Gas Component After Reaction | Methane |  |  | 70 ppm | 120 ppm | 70 ppm | 50 ppm |
|  | Ethane |  |  | 6 ppm | 8 ppm | 2 ppm | 3 ppm |
|  | Propane |  |  | 1 ppm | 2 ppm | 1 ppm | 1 ppm |
|  | Ethylene, Propylene |  |  | 30 ppm | 7 ppm | 2 ppm | 3 ppm |
|  | Carbon Monoxide |  |  | 1 ppm | 1 ppm | 1 ppm | 1 ppm |
|  | Hydrogen |  |  | — | — | — | — |

TABLE 3

|  |  |  |  | Comparative Example 1 | Comparative Example 2 | Comparative Example 3 | Comparative Example 4 | Comparative Example 5 | Comparative Example 6 |
|---|---|---|---|---|---|---|---|---|---|
| Substances Compounded | Water (ml) |  |  | 50 | 50 | 50 | 50 | 50 | 50 |
|  | Carbon Dioxide (Injection Time) |  |  | 3 minutes | 3 minutes | 3 minutes | 3 minutes | 3 minutes | 3 minutes |
|  | Hydrogen (Injection Time) |  |  |  | 3 minutes |  |  |  |  |
|  | Particle Body | Fe | 46 μm |  |  | 0.1 g |  |  |  |
|  |  |  | 36 μm |  |  |  | 0.1 g |  |  |
|  |  | Al | 100 μm |  |  |  |  | 0.1 g |  |
|  |  | Si | 300 μm |  |  |  |  |  | 0.1 g |

TABLE 3-continued

|  |  |  |  |  |  |  |  |  |
|---|---|---|---|---|---|---|---|---|
|  |  | Ti | 200 μm |  |  |  |  |  |
|  |  | Cu | 130 μm |  |  |  |  |  |
|  |  | Ni | 150 μm |  |  |  |  |  |
|  |  | Ba | 500 μm |  |  |  |  |  |
|  |  | Ca | 500 μm |  |  |  |  |  |
| Reaction Condition | Still Standing | Place |  | Indoor | Indoor | Outdoor | Outdoor | Outdoor | Outdoor |
|  |  | Time |  | 14 days | 7 days | 14 days | 14 days | 14 days | 14 days |
|  | Stir |  |  | no | no | no | no | no | no |
|  | Ceramic Beads | Zirconia 1.25 mm Alumina 0.5 mm |  | — — | — — | — — | — — | — — | — — |
| Detected Gas Component After Reaction | Methane |  |  | ND | ND | 8 ppm | 10 ppm | 2 ppm | 3 ppm |
|  | Ethane |  |  | ND | ND | ND | ND | ND | ND |
|  | Propane |  |  | ND | ND | ND | ND | ND | ND |
|  | Ethylene, Propylene |  |  | ND | ND | ND | ND | ND | ND |
|  | Carbon Monoxide |  |  | — | — | — | — | — | — |
|  | Hydrogen |  |  | ND | — | — | — | — | — |

|  |  |  |  | Comparative Example 7 | Comparative Example 8 | Comparative Example 9 | Comparative Example 10 | Comparative Example 11 |
|---|---|---|---|---|---|---|---|---|
| Substances Compounded | Water (ml) |  |  | 50 | 50 | 50 | 50 | 50 |
|  | Carbon Dioxide (Injection Time) |  |  | 3 minutes | 3 minutes | 3 minutes | 3 minutes | 3 minutes |
|  | Hydrogen (Injection Time) |  |  |  |  |  |  |  |
|  | Particle Body | Fe | 46 μm |  |  |  |  |  |
|  |  |  | 36 μm |  |  |  |  |  |
|  |  | Al | 100 μm |  |  |  |  |  |
|  |  | Si | 300 μm |  |  |  |  |  |
|  |  | Ti | 200 μm | 0.1 g |  |  |  |  |
|  |  | Cu | 130 μm |  | 0.1 g |  |  |  |
|  |  | Ni | 150 μm |  |  | 0.1 g |  |  |
|  |  | Ba | 500 μm |  |  |  | 0.1 g |  |
|  |  | Ca | 500 μm |  |  |  |  | 0.1 g |
| Reaction Condition | Still Standing | Place |  | Outdoor | Outdoor | Outdoor | Outdoor | Outdoor |
|  |  | Time |  | 14 days | 14 days | 14 days | 14 days | 14 days |
|  | Stir |  |  | no | no | no | no | no |
|  | Ceramic Beads | Zirconia 1.25 mm Alumina 0.5 mm |  | — — | — — | — — | — — | — — |
| Detected Gas Component After Reaction | Methane |  |  | ND | 1 ppm | ND | 6 ppm | 8 ppm |
|  | Ethane |  |  | ND | ND | ND | ND | ND |
|  | Propane |  |  | ND | ND | ND | ND | ND |
|  | Ethylene, Propylene |  |  | ND | ND | ND | ND | ND |
|  | Carbon Monoxide |  |  | — | — | — | — | — |
|  | Hydrogen |  |  | — | — | — | — | — |

TABLE 4

|  |  |  |  | Comparative Example 12 | Comparative Example 13 | Comparative Example 14 | Comparative Example 15 | Comparative Example 16 | Comparative Example 17 |
|---|---|---|---|---|---|---|---|---|---|
| Substances Compounded | Water (ml) |  |  | 50 | 50 | 50 | 50 | 50 | 50 |
|  | Carbon Dioxide (Injection Time) |  |  | 3 minutes | 3 minutes | 3 minutes | 3 minutes | 3 minutes | 3 minutes |
|  | Hydrogen (Injection Time) |  |  |  | 3 minutes | 3 minutes |  |  |  |
|  | Particle Body | Fe | 46 μm | 0.1 g |  | 0.1 g | 0.1 g |  |  |
|  |  |  | 36 μm |  | 0.1 g |  |  |  |  |
|  |  | Al | 100 μm |  |  |  |  | 0.1 g |  |
|  |  | Si | 300 μm |  |  |  |  |  | 0.1 g |
|  |  | Ti | 200 μm |  |  |  |  |  |  |
|  |  | Cu | 130 μm |  |  |  |  |  |  |
|  |  | Ni | 150 μm |  |  |  |  |  |  |
|  |  | Ba | 500 μm |  |  |  |  |  |  |
|  |  | Ca | 500 μm |  |  |  |  |  |  |
| Reaction Condition | Still Standing | Place |  | Indoor | Indoor | Outdoor | Outdoor | Outdoor | Outdoor |
|  |  | Time |  | 14 days | 14 days | 14 days | 14 days | 14 days | 14 days |
|  | Stir |  |  | no | no | yes | yes | yes | yes |
|  | Ceramic Beads | Zirconia 1.25 mm Alumina 0.5 mm |  | — — | — — | present — | present — | present — | present — |
| Detected Gas Component After Reaction | Methane |  |  | 9 ppm | 2 ppm | 7 ppm | 9 ppm | 2 ppm | 3 ppm |
|  | Ethane |  |  | ND | ND | ND | ND | ND | ND |
|  | Propane |  |  | ND | ND | ND | ND | ND | ND |
|  | Ethylene, Propylene |  |  | ND | ND | ND | ND | ND | ND |
|  | Carbon Monoxide |  |  | — | — | — | — | — | — |
|  | Hydrogen |  |  | — | — | — | — | — | — |

TABLE 4-continued

| | | | | Comparative Example 18 | Comparative Example 19 | Comparative Example 20 | Comparative Example 21 | Comparative Example 22 |
|---|---|---|---|---|---|---|---|---|
| Substances Compounded | Water (ml) | | | 50 | 50 | 50 | 50 | 50 |
| | Carbon Dioxide (Injection Time) | | | 3 minutes | 3 minutes | 3 minutes | 3 minutes | 3 minutes |
| | Hydrogen (Injection Time) | | | | | | | |
| | Particle Body | Fe | 46 μm | | | | | |
| | | | 36 μm | | | | | |
| | | Al | 100 μm | | | | | |
| | | Si | 300 μm | | | | | |
| | | Ti | 200 μm | 0.1 g | | | | |
| | | Cu | 130 μm | | 0.1 g | | | |
| | | Ni | 150 μm | | | 0.1 g | | |
| | | Ba | 500 μm | | | | 0.1 g | |
| | | Ca | 500 μm | | | | | 0.1 g |
| Reaction Condition | Still Standing | | Place | Outdoor | Outdoor | Outdoor | Outdoor | Outdoor |
| | | | Time | 14 days | 14 days | 14 days | 14 days | 14 days |
| | Stir | | | yes | yes | yes | yes | yes |
| | Ceramic Beads | Zirconia 1.25 mm | | present | present | present | present | present |
| | | Alumina 0.5 mm | | — | — | — | — | — |
| Detected Gas Component After Reaction | Methane | | | ND | 1 ppm | ND | 6 ppm | 8 ppm |
| | Ethane | | | ND | ND | ND | ND | ND |
| | Propane | | | ND | ND | ND | ND | ND |
| | Ethylene, Propylene | | | ND | ND | ND | ND | ND |
| | Carbon Monoxide | | | — | — | — | — | — |
| | Hydrogen | | | — | — | — | — | — |

Examples and comparative examples will be explained below.

The materials used are described below.

Pure water was used for water, and pure gasses were used for carbon dioxide and hydrogen.

Magnesium (Mg) used was manufactured by NACALAI TESQUE, INC., was particulate, and had a size of 414 μm, 371 μm, or 18 μm. Note that the size of the particles including those explained below was the average value of the sizes of 20 particles (maximum diameter of each particle) measured using a stereomicroscope or a scanning electron microscope (SEM).

Magnesium oxide (MgO), magnesium hydroxide (Mg(OH)$_2$), magnesium carbonate (MgCO$_3$), and basic magnesium carbonate (Mg(OH)$_2$.MgCO$_3$) used were manufactured by Tomita Pharmaceutical Co., Ltd., were particulate, and had a size of 150 μm.

Iron (Fe) used was manufactured by Wako Pure Chemical Industries, Ltd., was particulate, and had a size of 46 μm or 36 μm.

Aluminum (Al) used was manufactured by Wako Pure Chemical Industries, Ltd., was particulate, and had a size of 100 μm.

Barium (Ba) used was manufactured by Wako Pure Chemical Industries, Ltd., was particulate, and had a size of 500 μm.

Calcium (Ca) used was manufactured by Wako Pure Chemical Industries, Ltd., was particulate, and had a size of 500 μm.

Silicon (Si) used was manufactured by KINSEI MATEC CO., LTD., was particulate, and had a size of 300 μm.

Titanium (Ti) used was manufactured by FUKUDA METAL FOIL & POWDER CO., LTD., was particulate, and had a size of 200 μm.

Copper (Cu) used was manufactured by FUKUDA METAL FOIL & POWDER CO., LTD., was particulate, and had a size of 130 μm.

Nickel (Ni) used was manufactured by FUKUDA METAL FOIL & POWDER CO., LTD., was particulate, and had a size of 150 μm.

As ceramic beads, zirconia beads having a particle size of 1.25 mm (manufactured by Saint-Gobain K.K.), and alumina beads having a particle size of 0.5 mm (manufactured by TAIMEI CHEMICALS CO., LTD.) were used.

As a reaction container, a vial made of colorless and transparent glass (volume: 110 mL, diameter: 40 mm, and height: 125 mm) was used. The vial was plugged with a cap composed of an outer cap made of resin and having a hole in its central part and an inner cap made of rubber. By piercing a syringe needle into the inner cap, gas can be collected from a head space inside the vial.

Gas components were analyzed by gas chromatography (100HC, manufactured by NEW COSMOS ELECTRIC CO., LTD.).

Reactions of examples and comparative examples were conducted as described below.

In Example 1, 50 mL of water (pure water) was charged into a vial, and then 0.1 g of magnesium particle bodies having a size of 414 μm were added into the vial. Next, through a tube inserted into the opening of the vial, carbon dioxide was injected (blown) into water from near the bottom in the vial for 3 minutes (flow rate: 0.8 L/minute) for bubbling. After that, the tube was removed from the vial, and then the vial was sealed with a cap. The vial was left still indoors (inside a room in which temperature had been adjusted to around 23° C.) for 14 days, and subjected to a reaction. After the reaction was completed, gas was collected from a head space inside the vial by using a syringe, and components of the gas were analyzed.

In Example 2, the reaction was conducted under the same conditions as in Example 1, except that the vial was not left still indoors, but was left still outdoors (on the rooftop of a building where the average temperature was around 19° C.) for 14 days.

In Examples 3 to 5, the reaction was conducted under the same conditions as in Example 1, except that the particle bodies were changed to those of magnesium having a size of 371 μm, and the vial was left still indoors for 3, 7, or 14 days.

In Example 6, the reaction was conducted under the same conditions as in Example 1, except that the particle bodies were changed to those of magnesium having a size of 371 μm, and the vial was left still in an indoor dark place for 3 days.

In Example 7, the reaction was conducted under the same conditions as in Example 1, except that the particle bodies were changed to those of magnesium having a size of 18 μm; an injection time of carbon dioxide was changed to 1 minute; and the vial was left still indoors for 7 days.

In Example 9, 50 mL of water (pure water) was charged into a vial, and then 0.1 g of magnesium oxide particle bodies were added into the vial. Next, through a tube inserted into the opening of the vial, carbon dioxide was injected into water from near the bottom in the vial for 3 minutes (flow rate: 0.8 L/min) for bubbling. Next, through the tube inserted into the opening of the vial, hydrogen was injected into water from near the bottom in the vial for 3 minutes (flow rate: 0.8 L/min) for bubbling. After that, the tube was removed from the vial, and then the vial was sealed with a cap. The vial was left still indoors (inside a room in which temperature had been adjusted to around 23° C.) for 7 days, and subjected to a reaction. After the reaction was completed, gas was collected from a head space inside the vial by using a syringe, and components of the gas were analyzed.

In Examples 10 to 12, the reaction was conducted under the same conditions as in Example 9, except that the particle bodies were changed to those of magnesium hydroxide, magnesium carbonate, or basic magnesium carbonate.

In Example 13, firstly, 30 g of zirconia beads were placed in a vial. 50 mL of water (pure water) was charged into the vial, and then 0.1 g of magnesium particle bodies having a size of 371 μm were added into the vial. Next, through a tube inserted into the opening of the vial, carbon dioxide was injected into water from near the bottom in the vial for 1 minute (flow rate: 0.8 L/min) for bubbling. After that, the tube was removed from the vial, and then the vial was sealed with a cap. The vial was left still indoors (inside a room in which temperature had been adjusted to around 23° C.) for 3 days, and subjected to a reaction. Note that, only for 24 hours in the 3 days, the vial was vertically shaken with a shaker (frequency of shaking: 10 time/sec). After the reaction was completed, gas was collected from a head space inside the vial by using a syringe, and components of the gas were analyzed.

In Example 14, the reaction was conducted under the same conditions as in Example 13, except that the zirconia beads were changed to alumina beads.

In Example 15, firstly, 30 g of zirconia beads were placed in a vial. 50 mL of water (pure water) was charged into the vial, and then 0.1 g of magnesium oxide particle bodies were added into the vial. Next, through a tube inserted into the opening of the vial, carbon dioxide was injected into water from near the bottom in the vial for 1 minute (flow rate: 0.8 L/min) for bubbling. Next, through the tube inserted into the opening of the vial, hydrogen was injected into water from near the bottom in the vial for 1 minute (flow rate: 0.8 L/min) for bubbling. After that, the tube was removed from the vial, and then the vial was sealed with a cap. The vial was left still indoors (inside a room in which temperature had been adjusted to around 23° C.) for 3 days, and subjected to a reaction. Note that, only for 24 hours in the 3 days, the vial was vertically shaken with a shaker (frequency of shaking: 10 time/sec). After the reaction was completed, gas was collected from a head space inside the vial by using a syringe, and components of the gas were analyzed.

In Examples 16 to 18, the reaction was conducted under the same conditions as in Example 15, except that the particle bodies were changed to those of magnesium hydroxide, magnesium carbonate, or basic magnesium carbonate.

In Comparative Example 1, the reaction was conducted under the same conditions as in Example 1, except that no particle body was placed in a vial.

In Comparative Example 2, the reaction was conducted under the same conditions as in Example 9, except that no particle body was placed in a vial.

In Comparative Examples 3 to 11, the reaction was conducted under the same conditions as in Example 2, except that the particle bodies were changed to those of iron, aluminum, silicon, titanium, copper, nickel, barium, or calcium, having a size of 46 μm or 36 μm.

In Comparative Examples 12 and 13, the reaction was conducted under the same conditions as in Example 9, except that the particle bodies were changed to those of iron having a size of 46 μm or 36 μm, and the vial was left still indoors for 14 days.

In Comparative Examples 14 to 22, the reaction was conducted under the same conditions as in Example 13, except that the particle bodies were changed to those of iron, aluminum, silicon, titanium, copper, nickel, barium, or calcium, having a size of 46 μm or 36 μm; an injection time of carbon dioxide was changed to 3 minutes; and the vial was left still outdoors for 14 days (however, only for 24 hours in the 14 days, the vial was vertically shaken with a shaker (frequency of shaking: 10 time/sec)).

Examples 1 to 7, 13, and 14 conducted under the presence of magnesium showed larger methane concentrations at head spaces in vials than those of Comparative Examples 3, 4, 14, and 15 conducted under the presence of iron (about 140 times or greater), and thus methane was obtained at a high yield. In these Examples, hydrocarbons other than methane, such as ethane, propane, ethylene, and propylene were also able to be obtained.

Examples 13 and 14 in which a 24 hour-stir with ceramic beads was performed showed larger methane concentrations at head spaces in vials than those of Examples 1 to 8 in which a stir with ceramic beads was not performed, and thus methane was obtained at a high yield.

Examples 9 to 12, and 15 to 18 conducted under the presence of magnesium oxide, magnesium hydroxide, magnesium carbonate, or basic magnesium carbonate showed larger methane concentrations at head spaces in vials than those of Comparative Examples 12 and 13 conducted under the presence of iron (about 3 times or greater), and thus methane was obtained at a high yield. In these Examples, hydrocarbons other than methane, such as ethane, propane, ethylene, and propylene were also able to be obtained.

Examples 15 to 18 in which a 24 hour-stir with ceramic beads was performed showed larger methane concentrations at head spaces in vials than those of Examples 9 to 12 in which a stir with ceramic beads was not performed, and thus methane was obtained at a high yield.

In any of Examples 1 to 18, the hydrocarbon was generally able to be obtained at a high yield under the condition of an ordinary temperature and an ordinary pressure. Accordingly, external controls for heating or cooling and for pressurization or depressurization are not always required to obtain the given amount of a hydrocarbon, and thus, for example, reaction equipment can be simplified to lower cost in a practical use.

Based on Examples 1 to 18, in order to further study suitability of the hydrogen injection, reduction in sizes of ceramic beads, shortening of reaction time, increase of the yield of a hydrocarbon, and the like when a magnesium compound is used, Examples 19 to 26 were conducted and analyses were carried out. Each of the conditions and analysis results of gas components are shown in Table 5. In any of the Examples, external controls for heating or cooling and for pressurization or depressurization were not performed, and reactions were conducted under the atmosphere of an ordinary temperature and an ordinary pressure. The ordinary temperature and ordinary pressure are explained in Examples 1 to 18.

g of magnesium oxide particle bodies were added into the vial. Next, through a tube inserted into the opening of the vial,

TABLE 5

|  |  |  |  | Example 19 | Example 20 | Example 21 | Example 22 |
|---|---|---|---|---|---|---|---|
| Substances Compounded | Water (ml) |  |  | 90 | 90 | 90 | 90 |
|  | Carbon Dioxide (Injection Time) |  |  | 1 minute | 1 minute | 1 minute | 1 minute |
|  | Hydrogen (Injection Time) |  |  |  | 1 minute |  |  |
|  | Particle Body | Mg | 414 μm |  |  |  |  |
|  |  |  | 371 μm |  |  |  |  |
|  |  |  | 18 μm |  |  |  |  |
|  |  | MgO | 150 μm | 0.2 g | 0.2 g | 0.2 g |  |
|  |  | Mg(OH)$_2$ | 150 μm |  |  |  | 0.6 g |
|  |  | MgCO$_3$ | 150 μm |  |  |  |  |
|  |  | Mg(OH)$_2$·MgCO$_3$ | 150 μm |  |  |  |  |
| Reaction Condition |  | Place |  | Indoor | Indoor | Indoor | Indoor |
|  |  | Time |  | 1 day | 1 day | 1 day | 1 day |
|  |  | Stir |  | yes | yes | no | yes |
|  |  | Ceramic Beads | Zirconia 0.5 mm | present | present | — | present |
|  |  |  | Alumina 0.5 mm | — | — | — | — |
| Detected Gas Component After Reaction |  | Methane |  | 2586 ppm | 157 ppm | 27 ppm | 590 ppm |
|  |  | Ethane |  | — | — | — | — |
|  |  | Propane |  | — | — | — | — |
|  |  | Ethylene, Propylene |  | — | — | — | — |
|  |  | Carbon Monoxide |  | 15 ppm | 9 ppm | 8 ppm | 6 ppm |
|  |  | Hydrogen |  | — | — | — | — |
|  |  |  |  | Example 23 | Example 24 | Example 25 | Example 26 |
| Substances Compounded | Water (ml) |  |  | 90 | 90 | 90 | 90 |
|  | Carbon Dioxide (Injection Time) |  |  | 1 minute | 1 minute | 1 minute | 1 minute |
|  | Hydrogen (Injection Time) |  |  |  |  |  |  |
|  | Particle Body | Mg | 414 μm |  |  |  |  |
|  |  |  | 371 μm |  | 0.2 g | 0.4 g | 0.2 g |
|  |  |  | 18 μm |  |  |  |  |
|  |  | MgO | 150 μm |  |  |  | 0.2 g |
|  |  | Mg(OH)$_2$ | 150 μm |  |  |  |  |
|  |  | MgCO$_3$ | 150 μm | 0.6 g |  |  |  |
|  |  | Mg(OH)$_2$·MgCO$_3$ | 150 μm |  |  |  |  |
| Reaction Condition |  | Place |  | Indoor | Indoor | Indoor | Indoor |
|  |  | Time |  | 1 day | 1 day | 1 day | 1 day |
|  |  | Stir |  | yes | yes | yes | yes |
|  |  | Ceramic Beads | Zirconia 0.5 mm | present | present | present | present |
|  |  |  | Alumina 0.5 mm | — | — | — | — |
| Detected Gas Component After Reaction |  | Methane |  | 122 ppm | 3583 ppm | 4776 ppm | 6042 ppm |
|  |  | Ethane |  | — | — | — | — |
|  |  | Propane |  | — | — | — | — |
|  |  | Ethylene, Propylene |  | — | — | — | — |
|  |  | Carbon Monoxide |  | 12 ppm | 4 ppm | 4 ppm | 4 ppm |
|  |  | Hydrogen |  | — | — | — | — |

The materials used were the same as those described in Examples 1 to 18, except that zirconia beads having a particle size of 0.5 mm (manufactured by Saint-Gobain K.K.) were used as ceramic beads.

As a reaction container, a vial made of colorless and transparent glass and having a size different from that of the vial used in Examples 1 to 18 (volume: 150 mL, diameter: 50 mm, and height: 95 mm) was used. The vial was plugged with a cap composed of an outer cap made of resin and having a hole on its central part and an inner cap made of rubber. By piercing a syringe needle into the inner cap, gas can be collected from a head space inside the vial. The vial was fixed on a metal plate (a stainless steel plate having a thickness of 3 mm) to prevent seal leakage.

As in Examples 1 to 18, gas components were analyzed by gas chromatography (100HC, manufactured by NEW COSMOS ELECTRIC CO., LTD.).

Reactions of Examples 19 to 26 were conducted as described below.

In Example 19, firstly, 30 g of zirconia beads having a particle size of 0.5 mm were placed in an 150 mL vial. 90 mL of water (pure water) was charged into the vial, and then 0.2 carbon dioxide was injected into water from near the bottom in the vial for 1 minute (flow rate: 0.8 L/min) for bubbling. Hydrogen was not injected. After that, the tube was removed from the vial, and then the vial was sealed with a cap. A reaction was conducted while the vial was vertically shaken indoors (inside a room in which temperature had been adjusted to around 23° C.) with a shaker (frequency of shaking: 10 time/sec) for 1 day. After the reaction was completed, gas was collected from a head space inside the vial by using a syringe, and components of the gas were analyzed.

In Example 20, the reaction was conducted under the same conditions as in Example 19, except that, after bubbling of carbon dioxide, through a tube inserted into the opening of the vial, hydrogen was injected into water from near the bottom in the vial for 1 minute (flow rate: 0.8 L/min) for bubbling.

In Example 21, the reaction was conducted under the same conditions as in Example 19, except that zirconia beads were not placed, and the vial was left still without shaking.

In Example 22, the reaction was conducted under the same conditions as in Example 19, except that the particle bodies were changed to 0.6 g of magnesium hydroxide.

In Example 23, the reaction was conducted under the same conditions as in Example 19, except that the particle bodies were changed to 0.6 g of magnesium carbonate.

In Example 19, magnesium oxide was used as in Example 15; however, Example 19 is largely different from Example 15, particularly in that hydrogen was not injected and smaller zirconia beads were used. Although the reaction time was shortened to 1 day, the concentration of methane was larger (about 35 times or greater), that is, methane was obtained at a high yield. Compared to Example 19, the concentration of methane decreased in Example 20, in which hydrogen was injected. Compared to Example 19, the concentration of methane decreased also in Example 21, in which zirconia beads were not used, and the vial was not shaken.

In Example 22, magnesium hydroxide was used as in Example 16; however, Example 22 is largely different from Example 16, particularly in that hydrogen was not injected and smaller zirconia beads were used. Although reaction time was shortened to 1 day, the concentration of methane was larger (about 5 times), that is, methane was obtained at a high yield.

In Example 23, magnesium carbonate was used as in Example 17; however, Example 23 is largely different from Example 17, particularly in that hydrogen was not injected and smaller zirconia beads were used. Although reaction time was shortened to 1 day, the concentration of methane was larger, that is, methane was obtained at a high yield.

The above results indicate that, firstly, a hydrogen gas does not need to be injected even when a magnesium compound is used, and the yield of methane is high rather without the injection of a hydrogen gas. This can be discussed as follows.

In Examples 15 to 17, the injection of the hydrogen gas might work positively as allowing the magnesium compound to be in a transition state in which the magnesium compound has hydrogen. However, it might also work negatively such that part of carbon dioxide injected and dissolved in advance was removed, and thus the yield of methane was not so high.

In contrast, it is considered that in Examples 19 and 21 to 23, hydrogen generated by the reaction between the magnesium compound and water was attached to the magnesium compound so that the magnesium compound was brought into the transition state without the injection of hydrogen. Since the magnesium compound such as magnesium oxide has excellent reactivity such as an adsorptive property, it is used as a carrier for a catalyst. Thus, the magnesium compound is considered to be easily reacted with water covering its surface, compared with the case using a highly spreadable hydrogen gas. Furthermore, it is considered that carbon dioxide was not removed because hydrogen was not injected, and thus the yield of methane increased. Accordingly, by using water, which is less expensive, as a hydrogen source instead of a hydrogen gas, methane can be synthesized with a lower cost.

The above results indicate that, secondly, by the use of ceramic beads having a particle size close to that of a magnesium compound, the yield of methane is high compared to the case of using ceramic beads having a particle size much larger than that of a magnesium compound. This will be discussed below.

In Examples 15 to 17, it is considered that the particle size of the zirconia beads were 1.25 mm, which was much larger than 150 μm that was the particle size of magnesium oxide, so that the zirconia beads were not able to efficiently crush and grind the magnesium compound in the stirring step. In contrast, in Examples 19, 22, and 23, it is considered that, the particle size of the zirconia beads was 0.5 mm, which was close to 150 μm that was the particle size of magnesium oxide, so that the zirconia beads were able to efficiently crush and grind the magnesium compound in the stirring step to further enhance the reactivity of the magnesium compound.

In Example 24, the reaction was conducted under the same conditions as in Example 19, except that the particle bodies were changed to 0.2 g of magnesium.

In Example 25, the reaction was conducted under the same conditions as in Example 19, except that the particle bodies were changed to 0.4 g of magnesium.

In Example 26, the reaction was conducted under the same conditions as in Example 19, except that the particle bodies were changed to the mixture of 0.2 g of magnesium and 0.2 g of magnesium oxide.

In Example 24, magnesium was used, and its conditions were similar to those of Example 13; however, although reaction time was shortened to 1 day, the concentration of methane was not much decreased. This is also considered to be resulted from the effect of particle size of the zirconia beads, which was close to the particle size of magnesium, as described above. Accordingly, the particle size of a ceramic bead may preferably be 1 time to 6 times, and more preferably 1.3 times to 3.5 times that of a magnesium compound. In Example 25, the amount of magnesium was increased from that of Example 24, and the concentration of methane was larger. In Example 26 in which magnesium oxide was added with the amount of magnesium being the same as that of Example 24, the concentration of methane was even larger.

It is evaluated that in any of Examples 19 to 26, the hydrocarbon was generally able to be obtained at a high yield under the condition of an ordinary temperature and an ordinary pressure. Accordingly, external controls for heating or cooling and for pressurization or depressurization are not always required to obtain the given amount of a hydrocarbon, and thus, for example, reaction equipment can be simplified to reduce cost in a practical use.

Note that the present invention is not limited to the above examples, and modification may be suitably made for practical use, without departing from the purpose of the present invention.

(1) Although all the reactions of the above examples were conducted under the atmosphere of an ordinary temperature and an ordinary pressure, the reactions may also be conducted under the atmosphere of a temperature and a pressure other than the ordinary temperature and the ordinary pressure. Two examples of the atmosphere of a temperature and a pressure other than the ordinary temperature and the ordinary pressure will be explained below.

> The atmosphere of a temperature and a pressure other than the ordinary temperature and the ordinary pressure is produced by, for example, a change in the temperature due to an exothermic or endothermic reaction, and a change in the pressure resulting from the change of the amount of the gas in the reaction container (production or degradation of the gas). In this example, the advantage described in the previous paragraph still can be obtained.
>
> The atmosphere of a temperature and a pressure other than the ordinary temperature and the ordinary pressure is produced by, for example, external controls for heating or cooling and for pressurization or depressurization.

(2) Although all the reactions of the above examples were conducted in water, water vapor may also be used. Two examples of using water vapor will be explained below.

> Magnesium or a magnesium compound is placed in the air containing carbon dioxide, and spraying water vapor or water to the magnesium or the magnesium compound to produce a hydrocarbon from the carbon dioxide.

A magnesium compound is placed in the air containing carbon dioxide and hydrogen, and spraying water vapor or water to the magnesium compound to produce a hydrocarbon from the carbon dioxide.

The invention claimed is:

1. A method for manufacturing a hydrocarbon, in which carbon dioxide is reduced to produce the hydrocarbon, the method comprising steps of:
contacting a magnesium material selected from the group consisting of metallic magnesium and a magnesium compound with liquid water and the carbon dioxide and reducing the carbon dioxide and
producing the hydrocarbon.

2. The method for manufacturing a hydrocarbon according to claim 1, wherein
in the contacting step, the hydrocarbon is produced by bringing the magnesium material into contact with the liquid water and generating hydrogen, and combining the generated hydrogen with the reduced carbon dioxide.

3. The method for manufacturing a hydrocarbon according to claim 1, wherein the magnesium material is selected from the group consisting of magnesium oxide, magnesium hydroxide, magnesium carbonate and basic magnesium carbonate.

4. The method for manufacturing a hydrocarbon according to claim 1, wherein the magnesium material is a particulate material.

5. The method for manufacturing a hydrocarbon according to claim 1, wherein the contacting step includes a stirring step of stirring the magnesium material in particulate form together with ceramic beads, the liquid water and the carbon dioxide.

6. The method for manufacturing a hydrocarbon according to claim 1, wherein the contacting step is conducted under an atmosphere of ordinary temperatures of 5° C. to 35° C. and ordinary pressures of 0.05 Mpa to 0.15 Mpa.

7. A method for manufacturing a hydrocarbon, in which carbon dioxide is reduced to produce the hydrocarbon, the method comprising steps of:
contacting the carbon dioxide and liquid water with a single particulate active material selected from the group consisting of metallic magnesium and a magnesium compound, and
generating hydrogen,
reducing the carbon dioxide, and
combining the generated hydrogen and the reduced carbon dioxide and producing the hydrocarbon.

8. The method for manufacturing a hydrocarbon according to claim 7, wherein the contacting step includes a stirring step of stirring the single particulate material, the liquid water and the carbon dioxide together with ceramic beads.

9. The method for manufacturing a hydrocarbon according to claim 7, wherein the contacting, dissolving, absorbing and reducing steps are carried out in an atmosphere of ordinary temperatures of 5° C. to 35° C. and ordinary pressures of 0.05 Mpa to 0.15 Mpa.

10. The method for manufacturing a hydrocarbon according to claim 7, wherein the single particulate material is selected from the group consisting of magnesium oxide, magnesium hydroxide, magnesium carbonate and basic magnesium carbonate.

11. A method for manufacturing a hydrocarbon comprising steps of:
contacting a surface of a particulate magnesium material with liquid water and carbon dioxide, the particulate magnesium material being selected from the group consisting of metallic magnesium and a magnesium compound, and simultaneously:
dissolving a part of the carbon dioxide in the liquid water;
absorbing the liquid water on the surface of the particulate magnesium material, the absorbed liquid water reacting with the particulate magnesium material and generating hydrogen; and
reducing the dissolved carbon dioxide contained in the liquid water and combining the reduced carbon dioxide with the hydrogen generated on the surface of the particulate magnesium material and producing the hydrocarbon.

12. The method for manufacturing a hydrocarbon according to claim 11, wherein the contacting step includes a stirring step of stirring the particulate magnesium material, the liquid water and the carbon dioxide together with ceramic beads.

13. The method for manufacturing a hydrocarbon according to claim 11, wherein the contacting, dissolving, absorbing and reducing are carried out in an atmosphere of ordinary temperatures of 5° C., to 35° C. and ordinary pressures of 0.05 Mpa to 0.15 Mpa.

14. The method for manufacturing a hydrocarbon according to claim 11, wherein the magnesium material is selected from the group consisting of magnesium oxide, magnesium hydroxide, magnesium carbonate and basic magnesium carbonate.

* * * * *